United States Patent [19]

Hakala et al.

[11] Patent Number: 4,635,639
[45] Date of Patent: Jan. 13, 1987

[54] MODULAR PHYSIOLOGICAL INSTRUMENT

[75] Inventors: Douglas T. Hakala, Bothell; Joseph M. Bocek, Seattle; James G. Osborn, Medina, all of Wash.

[73] Assignee: Physio-Control Corporation, Redmond, Wash.

[21] Appl. No.: 689,747

[22] Filed: Jan. 8, 1985

[51] Int. Cl.⁴ .......................... A61N 1/36; A61B 5/04
[52] U.S. Cl. .................................. 128/419 D; 128/696
[58] Field of Search ........... 128/419 D, 696, 708-709, 128/908

[56] References Cited

U.S. PATENT DOCUMENTS

| | | | |
|---|---|---|---|
| 3,547,108 | 12/1970 | Seiffert | 128/419 D |
| 3,703,900 | 11/1972 | Holznagel | 128/419 D |
| 3,794,841 | 2/1974 | Cosentino et al. | 128/908 |
| 3,814,105 | 6/1974 | Howard et al. | 128/419 D |
| 3,857,398 | 12/1974 | Rubin | 128/419 PG |
| 3,905,355 | 9/1975 | Brundy | 128/908 |
| 3,910,257 | 10/1975 | Fletcher et al. | 128/908 |
| 4,094,310 | 6/1978 | McEachern et al. | 128/419 D |
| 4,096,856 | 6/1978 | Smith et al. | 128/419 D |
| 4,300,166 | 11/1981 | Marey . | |
| 4,310,754 | 1/1982 | Check, Jr. . | |

OTHER PUBLICATIONS

Taylor, "A Wide Dynamic Range R-Wave Trigger", *J. Clinical Engineering*, vol. 4, No. 2, Apr.-Jun. 1979, pp. 131-134.

*Primary Examiner*—William E. Kamm
*Assistant Examiner*—Mitchell J. Shein
*Attorney, Agent, or Firm*—Christensen, O'Connor, Johnson & Kindness

[57] ABSTRACT

A physiological instrument that includes a first component comprising an ECG monitor and a second component comprising a defibrillator. The second component may also include a pacemaker mounted to and electrically connected with the defibrillator. The first and second components may communicate with one another entirely by means of three optical communication channels, each channel including an optical signal path that includes windows through which the optical signals pass into and out of the components. The components may therefore operate in a fully integrated manner despite the fact that no electrical signal path exists between the components. The communication channels include a serial channel through which information concerning defibrillator and pacemaker operation is transmitted to the ECG monitor, a tri-state channel through which sync and ECG source information is transmitted from the ECG monitor to the defibrillator/pacemaker, and an analog channel through which either an ECG signal from the defibrillator electrodes or an eyeclose signal from the pacemaker may be transmitted to the ECG monitor. Data transmitted through the serial channel includes a power-on signal, such that turning on the defibrillator automatically turns on the ECG monitor. The tri-state channel is used to transmit sync information when the ECG monitor determines that the defibrillator is on and when the defibrillator electrodes have not been selected as the ECG signal source. When the defibrillator is off, the ECG monitor controls the supply of power to the defibrillator electrode preamplifier via the tri-state channel.

14 Claims, 7 Drawing Figures

MODULAR PHYSIOLOGICAL INSTRUMENT

FIELD OF THE INVENTION

The present invention relates to physiological instruments and, in particular, to a modular physiological instrument having an EGG monitor component and a defibrillator/pacemaker component that are capable of both independent and integrated operation.

BACKGROUND OF THE INVENTION

An ECG monitor is a diagnostic instrument for providing a real-time or delayed display or a printed record of a patient's ECG waveform. The ECG monitor is typically interconnected with the patient via a set of electrodes and associated conductors commonly referred to as a patient cable. A defibrillator is a therapeutic instrument that is used to assist in curing certain cardiac irregularities, particularly ventricular and atrial fibrillation. The defibrillator is a therapeutic instrument that is used to assist in curing certain cardiac irregularities, particularly ventricular and atrial fibrillation. The defibrillator is typically interconnected with the patient via a set of large paddle electrodes and associated conductors, and operates to apply a high energy DC pulse to the patient via the paddle electrodes when appropriately triggered by an operator. The operator's decision to use defibrillation is typically based upon an examination of the patient's ECG waveform.

In one prior type of physiological instrument, an ECG monitor and a defibrillator are combined and electrically connected within a single housing. In such an instrument, circuitry is often provided to allow the ECG monitor to receive the ECG signal through the paddle electrodes that are normally associated with the defibrillator, rather than through the patient cable. Although the patient cable provides a better ECG signal, there is often an important speed advantage in using the paddle electrodes. Physiological instruments are also known in which the ECG monitor and defibrillator are modular units that are capable of operating either independently, or in an interconnected manner in which the defibrillator is mechanically and electrically connected to the ECG monitor.

A pacemaker is a therapeutic instrument that is connected to a patient through pacing electrodes and associated connectors, and operates to deliver a series of electrical pacing pulses to the patient. Each pacing pulse stimulates one heart contraction, and the pacing pulses are therefore delivered at a rate corresponding to the desired heart rate. A pacemaker may operate in either a nondemand mode, in which pacing pulses are delivered regardless of the patient's heart activity, or in a demand mode in which pacing pulses are only delivered if the patient's heart is not pumping properly. For demand pacing, an ECG monitor or its equivalent is required in order to monitor heart activity.

SUMMARY OF THE INVENTION

The present invention provides a physiological instrument that includes a first component comprising an ECG monitor and a second component comprising a defibrillator. The second component may also include a pacemaker mounted to and electrically connected with the defibrillator. The first and second components may communicate with one another entirely by means of three optical communication channels, each channel including an optical signal path that includes windows through which the optical signals pass into and out of the components. The components may therefore operate in a fully integrated manner despite the fact that no electrical signal path exists between the components.

In one aspect, the present invention provides a physiological instrument having a first component comprising an ECG monitor and a second component comprising a defibrillator. Each component includes means for permitting an operator to turn the components on and off, and the components are adapted for integrated operation wherein information concerning defibrillator operation is transmitted from the defibrillator to the ECG monitor. The defibrillator comprises means for generating a power-on signal when the defibrillator is turned on, and means for transmitting the power-on signal to the ECG monitor. The ECG monitor comprises means for receiving the power-on signal, and means responsive to receipt of the power-on signal for turning on the ECG monitor. In a preferred embodiment, the defibrillator generates a first electrical power-on signal that is converted to an optical signal that is transmitted out of the defibrillator through a window. The ECG monitor includes a window through which the optical signal may be transmitted into the ECG monitor, photoreceiver means for converting the optical signal into a second electrical power-on signal corresponding to the first electrical power-on signal, and means responsive to the second electrical power-on signal for turning on the ECG monitor. The power-on signal preferably comprises digital data that is transmitted in serial form. In a preferred embodiment, the digital data comprises at least one byte having a hexadecimal value of 55.

In another aspect, the components are adapted for integrated operation wherein information concerning defibrillator operation is transmitted from the defibrillator to the ECG monitor. The defibrillator comprises means for converting such information into a first electrical signal, phototransmitter means for converting the first electrical signal into a corresponding optical signal, and a window through which the optical signal may be transmitted out of the defibrillator. The ECG monitor comprises a window through which the optical signal may be transmitted into the ECG monitor, and photoreceiver means for converting the optical signal into a second electrical signal corresponding to the first electrical signal. The second component may further comprise a pacemaker, and the information transmitted from the defibrillator may include information concerning pacemaker operation.

In a further aspect, the present invention provides a physiological instrument that includes a first component comprising an ECG monitor adapted to process an ECG signal, and a second component comprising a defibrillator having a pair of electrodes and means for delivering a defibrillation shock to a patient through the electrodes. The components are adapted for integrated operation in which the defibrillator electrodes are the source of the ECG signal processed by the ECG monitor. The defibrillator comprises means for producing a first electrical ECG signal by means of the electrodes, and phototransmitter means for converting the first electrical ECG signal into a corresponding optical ECG signal. The ECG monitor comprises photoreceiver means for receiving the optical ECG signal and for converting it into a second ECG electrical signal corresponding to the first electrical ECG signal. Each component may comprise a window through which the optical signal may be transmitted from the defibrillator to the ECG monitor. The second component may further comprise a pacemaker operative to produce an electrical eyeclose signal, and means for selecting either the first electrical ECG signal or the eyeclose signal for conversion into the optical signal by the phototransmitter means.

In a further aspect of the present invention, the ECG monitor comprises means for generating an electrical first sync signal corresponding to a patient's R wave, and phototransmitter means for converting the first sync signal into a corresponding optical signal. The defibrillator comprises photoreceiver means for converting the optical signal into an electrical second sync signal corresponding to the first sync signal, and means for controlling the timing of a defibrillation shock based upon the second sync signal. The second component may further comprise a pacemaker that includes means for producing pacing pulses, and the pacemaker may include means for controlling the timing of the pacing pulses based upon the second sync signal.

In a further aspect of the present invention, the ECG monitor comprises means for processing an ECG signal, means for generating an electrical first sync signal corresponding to an R wave in the ECG signal, means for converting the first sync signal into a corresponding optical signal, means for permitting operator selection of the defibrillator electrodes as the source of the ECG signal, and means for detecting that the defibrillator has been turned on. The defibrillator comprises a power supply, means for delivering a defibrillation shock to the patient through the electrodes, preamplifier means for producing a first electrical ECG signal by means of the defibrillator electrodes, means for receiving the optical signal and converting the optical signal into an electrical second sync signal corresponding to the first sync signal, means for controlling the timing of a defibrillation shock based upon the second sync signal, and control means for supplying power from the power supply to the preamplifier means. The ECG monitor is adapted to produce the first electrical sync signal only when the defibrillator is on and the operator has not selected the electrodes as the source of the ECG signal. When the ECG monitor detects that the defibrillator is off, the ECG monitor modulates the optical signal with ECG source information indicating whether or not the defibrillator electrodes have been selected as the source of the ECG signal, and the defibrillator includes means responsive to the ECG source information for controlling the supply of power from the power supply to the preamplifier means.

DETAILED DESCRIPTION OF THE INVENTION

Figure 1:
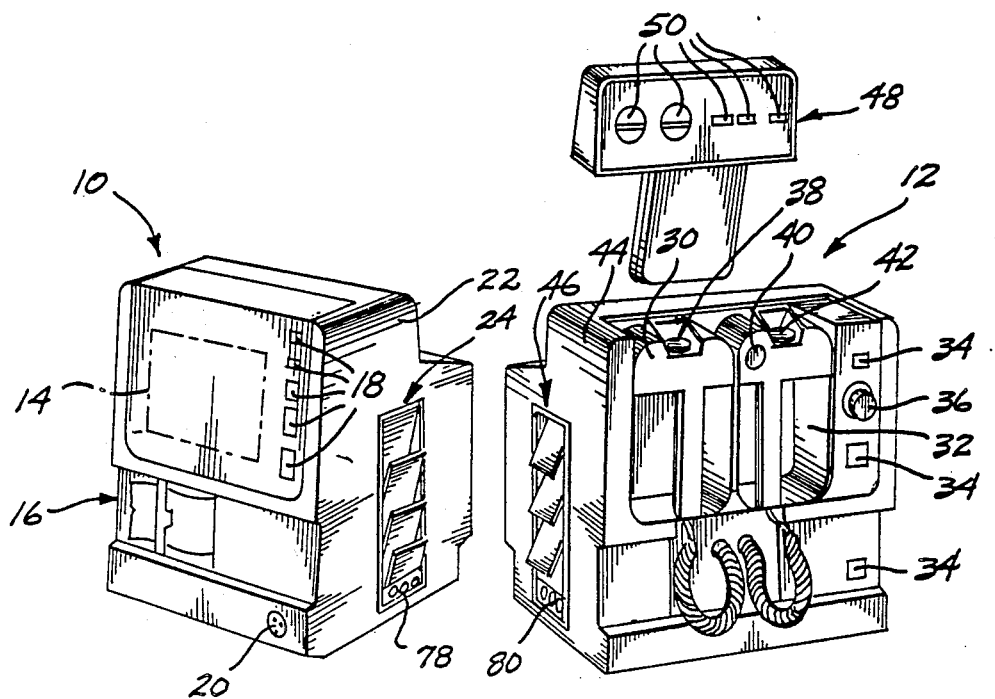
FIG. 1 is a perspective view of an ECG monitor, a defibrillator and a pacemaker that are adapted for integrated operation.

FIG. 1 illustrates a modular physiological instrument comprising ECG monitor 10, defibrillator 12, and pacemaker 48. ECG monitor 10 comprises display screen 14, recorder 16, push-button switches 18 and connector 20 for receiving a patient cable. ECG monitor 10 also includes side 22 having connector 24 formed therein. Display screen 14 provides a real-time or delayed display of a patient's ECG waveform. Recorder 16, when selected by the operator, provides a permanent record of the patient's ECG waveform and of related information. The electrical signal representing the patient's ECG waveform is provided either through the patient cable and connector 20, or via defibrillator 12 as described below.

Defibrillator 12 comprises paddle electrodes 30 and 32, push-button switches 34 and energy selector dial 36. Paddle electrode 32 includes charge switch 40, and paddle electrodes 30 and 32 comprise discharge switches 38 and 42 respectively. The defibrillator may be used by pressing charge switch 40 until the defibrillator energy storage means has charged, applying paddle electrodes 30 and 32 to a patient, and then simultaneously depressing discharge switches 38 and 42. The paddle electrodes may also be used to provide the ECG signal displayed or recorded by ECG monitor 10. The defibrillator includes side 44 having connector 46 formed therein. Connector 46 is adapted to mate with connector 24 of ECG monitor 10 in order to mechanically connect these components into a single unit.

Pacemaker 48 is adapted for mounting to the top of defibrillator 12, such that an electrical connector on the pacemaker engages a corresponding electrical connector on the defibrillator to establish electrical communication between these units. The pacemaker also includes a connector for receiving a pacing cable through which pacing pulses may be delivered to a patient, and rotary or pushbutton switches 50 that provide for operator selection of pacing mode, pacing rate and pacing start/stop.

Figure 2:
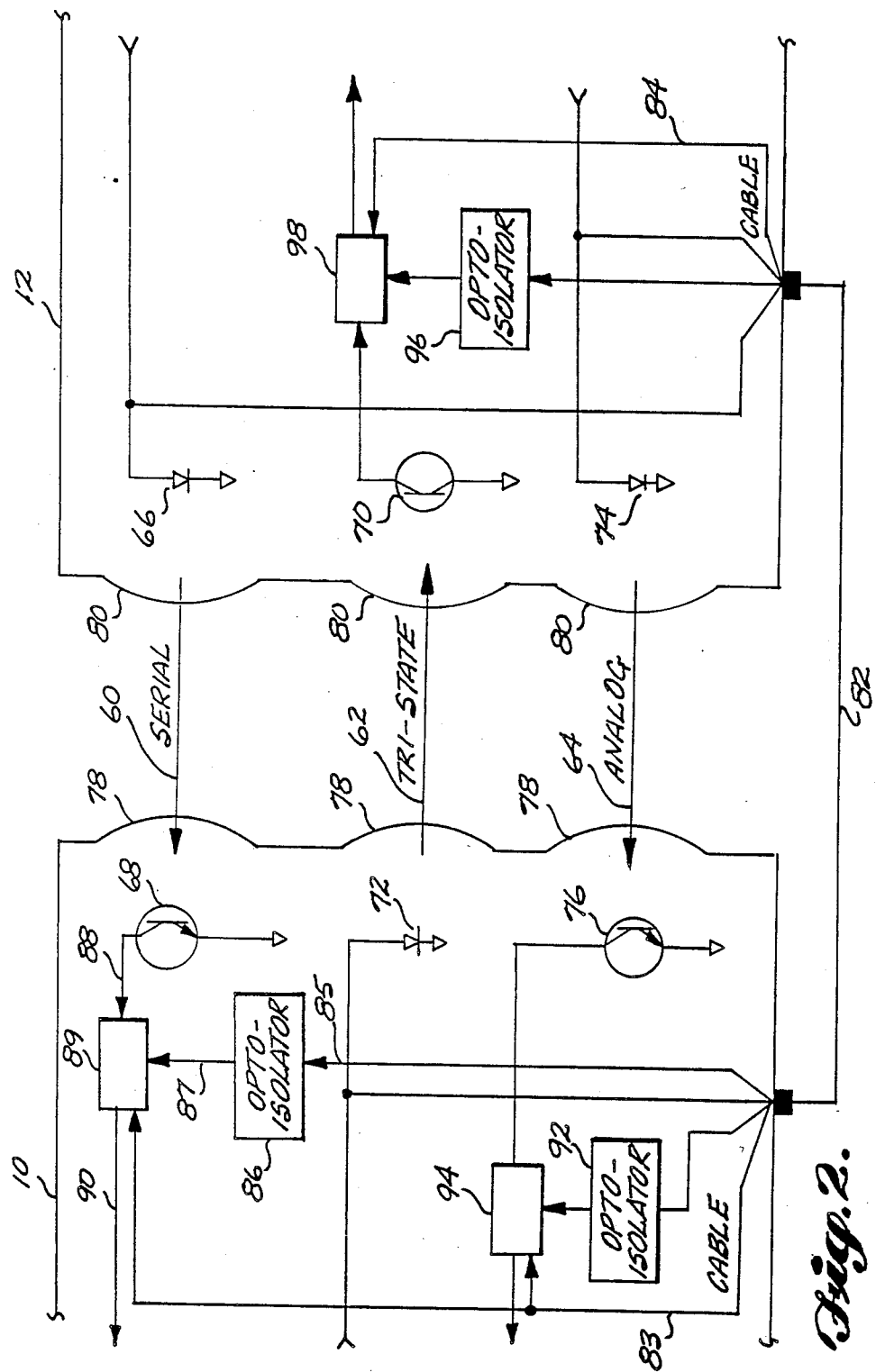
FIG. 2 is a schematic diagram illustrating the communication channels between the ECG monitor and the defibrillator.

All communication between ECG monitor 10 and defibrillator 12 is carried out via three communication channels. Referring to FIG. 2, these channels comprise serial channel 60, tri-state channel 62 and analog channel 64. Serial channel 60 and analog channel 64 are used to convey information from defibrillator 12 to ECG monitor 10. Tri-state channel 62 is used to convey information from ECG monitor 10 to defibrillator 12. Each channel comprises either an optical signal path or an optically isolated electrical signal path. The optical signal path for serial channel 60 comprises LED 66 in defibrillator 12 and phototransistor 68 in ECG monitor 10. The optical signal path for tri-state channel 62 comprises LED 72 in ECG monitor 10 and phototransistor 70 in defibrillator 12. The optical signal path for analog channel 64 comprises LED 74 in defibrillator 12 and phototransistor 76 in ECG monitor 10. Connector 24 of ECG monitor 10 comprises three windows 78 through which optical signals may pass to phototransistors 68 and 76 and from LED 72. Similarly, connector 46 of defibrillator 12 includes three windows 80 through which optical signals can pass from LEDs 66 and 74 and to phototransistor 70. Windows 78 and 80 are located in the lower portions of connectors 24 and 46 respectively (FIG. 1), such that windows 78 are adjacent to windows 80 when the ECG monitor and defibrillator components are mechanically connected. Therefore when the components are mechanically connected, all communication between the components may be carried out by means of optical signals passing through windows 78 and 80, and no electrical signal path between the components is required.

To provide for operation when the ECG monitor and defibrillator are not mechanically coupled, electrical signal paths for the serial, tri-state and analog channels may be provided via cable 82 that plugs into connectors in each component. Proper connection of cable 82 to both components results in a CABLE signal on line 83 in ECG monitor 10, and a similar CABLE signal on line 84 in defibrillator 12. The electrical signal path for serial channel 60 comprises line 85, opto isolator 86 and line 87. The optical signal path for the serial channel comprises line 88. Switch 89 selects either the electrical or optical signal path depending upon the presence or absence, respectively, of the CABLE signal on line 83, and connects the selected signal path to output line 90. In a similar manner, the electrical signal path for analog channel 64 comprises opto isolator 92, and switch 94 selects between the electrical and optical signal paths for the analog channel based upon the CABLE signal on line 83. In defibrillator 12, the electrical signal path for the tri-state channel comprises opto isolator 96, and switch 98 selects between optical and electrical paths for the tri-state channel based upon the CABLE signal on line 84.

Figure 3:
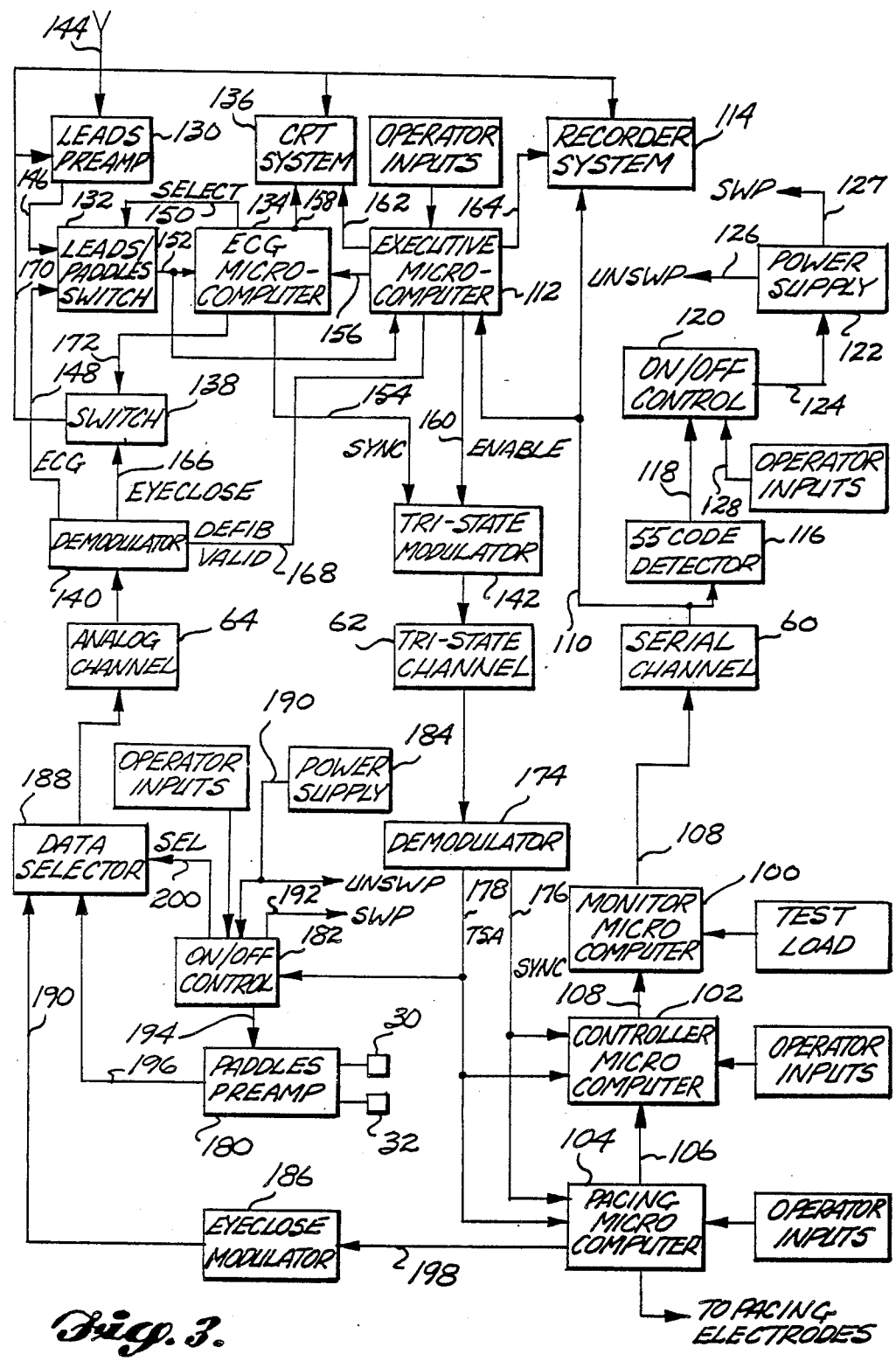
FIG. 3 is a block diagram of the components of the present invention.

FIG. 3 sets forth a block diagram of one preferred embodiment of the components of the ECG monitor, defibrillator and pacemaker components of the present invention. The upper portion of FIG. 3 illustrates ECG monitor 10, and the lower portion of FIG. 3 illustrates defibrillator 12 and pacemaker 48. Referring initially to the lower right-hand portion of FIG. 3, the defibrillator/pacemaker component comprises monitor microcomputer 100, controller microcomputer 102 and pacing microcomputer 104. Pacing micro-computer 104 is located in pacemaker 48. The pacing microcomputer receives user inputs via switches 50, such inputs including pacing rate, pacing mode and pacing start/stop. Pacing mode may be either demand or nondemand. Nondemand pacing denotes pacing that occurs continuously, at the selected pacing rate, without regard to that patient's intrinsic cardiac rhythm. In contrast, demand pacing is pacing that occurs only as needed or demanded. As described below, ECG monitor 10 analyzes the patient's ECG waveform and determines whether R wave activity is present. When the demand pacing mode has been selected, pacing microcomputer 104 will cause pacing pulses to occur at the selected pacing rate only when R wave activity is not sensed. Operation of the pacemaker is a demand pacing mode therefore requires information from ECG monitor 10 concerning the occurrence of R waves. As described below, this information is transmitted to defibrillator 12 and to pacemaker 48 via tri-state channel 62.

Controller microcomputer 102 receives operator inputs for defibrillation energy level, pacing current selection, sync mode selection, and charge and discharge commands. Such information is input by an operator by means of switches 34, energy selector dial 36, charge switch 40 and discharge switches 38 and 42 (FIG. 1). Sync mode refers to a form of defibrillation known as synchronized cardioversion in which the timing of the defibrillation discharge is controlled such that the discharge is are not delivered during a certain critical period following the patient's R wave. Operation of the defibrillator in sync mode therefore also requires information from the ECG monitor concerning the occurrence of R waves. Controller microcomputer 102 also receives information from the pacing microcomputer over serial communication line 106 that indicates current operator selections for pacing rate, pacing mode and pacing start/stop.

Monitor microcomputer 100 is responsible for determining that defibrillation discharges into the defibrillator's test load are executed properly, and of recording the results of such discharges. The monitor microcomputer also receives over serial communication line 108 all operator selections that have been input via the controller microcomputer or the pacing microcomputer. All such digital data including test load discharge data is serially transmitted by monitor microcomputer 100 to the ECG monitor over serial channel 60. In one preferred embodiment, this data is sent to the ECG monitor from the difibrillator at a rate of 244 baud organized as a packet of seven bytes that is sent once each 0.41 seconds. Each byte contains a start bit, eight data bits and a stop bit. For the optical signal path, "1" and "0" bits corresponding to LED 66 (FIG. 2) being driven full-off or full-on, respectively. On the ECG monitor side of communication channel 60, such information is routed via line 110 to executive microcomputer 112, recorder system 114, and 55 code detector 116. Executive microcomputer 112 coordinates the overall operation of the ECG monitor, and is described in greater detail below. Recorder system 114 includes recorder 16 (FIG. 1), together with a recorder microcomputer that controls recorder system operation and the formatting of information to be recorded. The information recorded by recorder 16 includes both the patient's ECG waveform plus annotations relating to defibrillator or pacemaker operations and operator selections, such as defibrillation energy selection, defibrillator firing (both test and actual), selection of sync mode, selection of pacing mode, pacing current and pacing rate. The data upon which such annotations are based is provided by the defibrillator via serial channel 60.

As indicated above in connection with FIG. 2, the components of the instrument of the present invention are adapted to operate in an optical communication mode in which there are no electrical signal paths and no auxiliary cables between the ECG monitor and defibrillator components. Each of such components therefore includes its own power supply. Power for ECG monitor 10 is provided by power supply 122, and power for defibrillator 12 and pacemaker 48 is provided by power supply 184. Both power supplies include both a battery and means for deriving power from an external AC line. Power supply 122 produces unswitched (i.e., always available) power on line 126, and switched power on line 127 that is provided only when the ECG monitor has been turned on. Power supply 184 produces unswitched power on line 190. Switched power for the defibrillator is provided through on/off control 182, as described in detail below.

In accordance with the present invention, means are provided whereby turning on defibrillator 12 also operates to turn on ECG monitor 10. When the defibrillator is turned on and switched power is applied to monitor microcomputer 100, the monitor microcomputer executes an initialization routine whereby a power-on signal comprising one or more bytes having the value 55 hex (10101010) are transmitted to the ECG monitor via serial channel 60. The resulting "55" byte on line 110 is detected by 55 code detector 116, and the 55 code detector responds by generating a wake-up signal on line 118 that is received by on/off control 120. On/off control 120 also receives on and off commands via line 128 as a result of operator actuation of switches 18 (FIG. 1). The on/off control and the 55 code detector are both supplied with unswitched power from power supply 122. When the ECG monitor is off, on/off control 120 controls power supply 122 such that switched power is not produced on line 127. However, in response to an appropriate signals on line 118 or line 128, on/off control 120 sends a signal to power supply 122 over line 124 that causes the power supply to apply power to line 126, turning on the ECG monitor.

ECG monitor 10 further comprises leads preamp 130, leads/paddle switch 132, ECG microcomputer 134, CRT system 136, switch 138, demodulator 140 and tri-state modulator 142. An ECG signal is normally provided to the ECG monitor through conventional 3 or 5 lead patient cables. Such an ECG signal enters the ECG monitor via connector 20 (FIG. 1) and is routed by line 144 to leads preamp 130. The leads preamp amplifies the signal on line 144, and also, electrically isolates line 144 and the patient cable from the remainder of the ECG monitor. Leads preamp 130 outputs its amplified (leads) ECG signal on line 146. Leads/paddles switch 132 receives the leads ECG signal on line 146, and may also receive a paddles ECG signal from defibrillator 12 via line 148. The derivation of the ECG signal on line 148 is described below. Leads/paddle switch 132 selects either the leads or paddles ECG signal in response to a select signal from ECG microcomputer 134 via line 150, and outputs the selected ECG signal on line 152. The ECG signal on line 152 is sent to ECG microcomputer 134 and to executive microcomputer 112.

The executive microcomputer receives inputs from the operator via switches 18 (FIG. 1), and controls the mode logic of the ECG monitor. For example, executive microcomputer 112 receives operator information specifying the type of patient cable (e.g. 3 lead or 5 lead) attached to connector 20, whether such leads or the defibrillator paddle electrodes should be used as the source of the ECG signal, whether recorder 16 should operate, and the rate at which CRT system 136 should operate. The executive microcomputer also digitizes the analog ECG signal on line 152 for display by CRT system 136 and for use by recorder system 114. The digitized ECG data is sent from executive microcomputer 112 to the CRT system via data path 162, and to the recorder system via data path 164. The executive microcomputer also monitors the serial data stream on line 110 in order to determine whether the defibrillator is on and transmitting data to the ECG monitor. Information concerning the presence or absence of serial data is sent from the executive microcomputer to the ECG microcomputer via line 156. The executive microcomputer also controls the enable signal on line 160 based upon the presence or absence of serial data, as described below.

ECG microcomputer 134 digitizes the analog ECG signal on line 152 exclusively for the purpose of R wave detection. When the ECG microcomputer detects an R wave, it may send a sync pulse to tri-state modulator 142 over line 154. A similar sync pulse is also output to CRT system 136 over line 158. The sync pulse is used by the CRT system to place a symbol on the CRT display corresponding to a detected R wave. The ECG microcomputer also issues an appropriate select signal on line 150 in response to information from the executive microcomputer via line 156 that indicates the current operator selection for the ECG signal source.

Tri-state channel 62 is used to send sync pulses detected by ECG microcomputer 134 to the defibrillator, and is also used to control the supply of power to portions of the difibrillator 12 when the defibrillator is off. The signal on tri-state channel 62 has three states: (a) 0 Hz (always off); (b) 8 kHz; or (c) 32 kHz. The tri-state modulator selects one of these states in response to the enable signal from executive microcomputer 112 on line 160 and the sync signal from ECG microcomputer 134 via line 154. In particular, when executive microcomputer 112 determines that serial data is being received from the defibrillator via serial channel 60 and that paddles have not been selected as the ECG signal source, it issues an enable signal on line 160 that enables tri-state modulator to produce states (b) and (c). The selection between states (b) and (c) is then based upon the sync pulse received from the ECG microcomputer. The tri-state modulator will hold the signal on tri-state channel 62 in state (b) except during the occurrence of a sync pulse, during which time it will switch the signal to state (c). When serial data is being received and paddles have been selected, the executive microcomputer uses an enable signal that forces the tri-state modulator to produce state (a). When serial data is not being received from the defibrillator over serial channel 60, executive microcomputer controls the tristate modulator, via enable line 160, based upon whether the operator has selected the defibrillator paddles or the ECG patient cable as the source of the ECG signal. In particular, while any ECG source except for defibrillator paddles is selected, the executive microcomputer causes the signal on tri-state channel 62 to be in state (a). However if the defibrillator paddles are selected, the executive microcomputer enables state (b). This information is used by the defibrillator to control application of electrical power to the paddles preamplifier when the defibrillator is off, as described below.

The information transmitted to the defibrillator via tri-state channel 62 is demodulated by demodulator 174, to produce a sync signal on line 176 and a tri-state active (TSA) signal on line 178. The tri-state active signal is described in greater detail below. The sync signal is sent to controller microcomputer 102 and pacing microcomputer 104. The pacing microcomputer uses the sync signal during demand pacing to decide whether or not a pacing pulse should be delivered to the patient. The controller microcomputer uses the sync signal whenever the operator has selected sync (synchronized cardioversion) mode for the defibrillator.

Defibrillator 12 further comprises paddles preamp 180, on/off control 182, power supply 184, eyeclose modulator 186 and data selector 188. Demodulator 174 produces a tri-state active signal on line 178 whenever an 8 or 32 kHz signal is being received over tri-state channel 62, i.e., whenever the tri-state signal is in states (b) or (c). The tri-state active signal is sent to controller microcomputer 102, pacing microcomputer 104 and on/off control 182. The controller microcomputer permits an operator to select sync mode only when the tri-state active signal is present. The pacing microcomputer permits an operator to start pacing only when the tri-state active signal is present.

When the defibrillator is off, the tri-state active signal indicates whether or not paddles have been selected as the ECG signal source, and is used to control the supplying of power to paddles preamp 180. Power supply 184 generates unswitched power on line 190 that is input to on/off control 182 and is also supplied to demodulator 174 and to other defibrillator components which are always powered. On/off control 182 connects the unswitched power on line 190 to switched power line 192 in response to operator inputs via switches 34 (FIG. 1). On/off control 182 also connects the unswitched power on line 190 to paddles preamp 180 via line 194 in response to operator inputs and to the tri-state active signal on line 178. In particular, when the defibrillator is on, power is supplied to paddle preamp 180 regardless of the tri-state active signal. However when the defibrillator is off, the paddles preamp is supplied with power whenever the tri-state active signal is present, i.e., whenever the operator selects paddles as the ECG input source via switches 18 on the ECG monitor.

Paddles preamp 180 receives the ECG signal from paddle electrodes 30 and 32, and amplifies such signal by a gain of approximately 500. The paddles preamp then uses the amplified signal to modulate the frequency of a 15 kHz carrier signal, and the modulated signal is sent to switch 188 via line 196. The other input to data selector 188 is a modulated eyeclose signal on line 190 produced by eyeclose modulator 186. Eyeclose refers to a signal generated by pacing microcomputer 104 on line 198. The eyeclose signal comprises a pulse that is essentially simultaneous with but slightly longer than the pacing pulse produced by the pacing microcomputer. The eyeclose signal is used to protect leads preamp 130 from voltage transients that can be produced in the ECG patient cable by a pacing pulse. In particular, the eyeclose signal shunts high voltage signals that are received by the front end filter of leads preamp 130. The eyeclose signal generated by the pacing microcomputer on line 198 is frequency modulated by eyeclose modulator 186, and the frequency modulated signal is sent to data selector 188 over line 190.

Data selector 188 sends either the eyeclose signal on line 190 or the ECG signal on line 196 to the ECG monitor via analog channel 64. The signal selected by data selector 188 is controlled by a select signal generated by on/off control 182 on line 200. As described in greater detail below, on/off control 182 will cause the ECG signal on line 196 to be selected whenever the defibrillator is off or the tri-state active signal is not present. In all other instances, data selector 188 will select the modulated eyeclose signal on line 190.

The data transmitted to the ECG monitor via analog channel 64 is demodulated by demodulator 140. Demodulator 140 produces an analog ECG signal on line 148, an eyeclose signal on line 166, and a defib valid signal on line 168. The ECG signal on line 148 forms one of the inputs to leads/paddle switch 132, as described above. The eyeclose signal on line 166 is input to switch 138. Switch 138 passes the eyeclose signal to line 170 in response to an eyeclose enable signal from ECG microcomputer 134 over line 172. The ECG microcomputer issues the eyeclose enable signal whenever paddles have not been selected as the ECG source, such information being provided to the ECG microcomputer by the executive microcomputer via line 156. The eyeclose signal on line 170 is sent to leads preamp 130, CRT system 136 and recorder system 114. The eyeclose signal blocks the large voltage transients that may occur on line 144 during a pacing pulse, as described above. The CRT and recording systems use the eyeclose signal to respectively display and record the occurrence of a pacing pulse. The defib valid signal is used by the executive microcomputer to determine whether the defibrillator is transmitting information to the ECG monitor via analog channel 64. If the defib valid signal is not present, the executive microcomputer will not permit the operator to select paddles as the ECG signal source. Loss of the defib valid signal will also cause the executive microcomputer to display a "signal lost" signal on display screen 14 of CRT system 136.

The function of the three communication channels between the ECG monitor and the defibrillator may be summarized as follows. Serial channel 60 is used to convey defibrillation and pacing information to the ECG monitor for use by CRT system 136 and recorder system 114. The presence or absence of serial data on serial channel 60 is also sensed by executive microcomputer 112, and used to determine whether or not the difibrillator is on. When the defibrillator is on and paddles have not been selected, tri-state channel 62 is used to convey sync pulses (corresponding to a patient's R wave) to the defibrillator for use in demand pacing or synchronized cardioversion. When the defibrillator is off, the tri-state modulator is used to indicate whether paddles have been selected as the ECG signal source. When paddles have been selected, the defibrillator responds by supplying power to paddles preamp 180. Finally, analog channel 64 is used to convey either the paddles ECG signal, or an eyeclose signal, to the ECG monitor.

Figure 4:
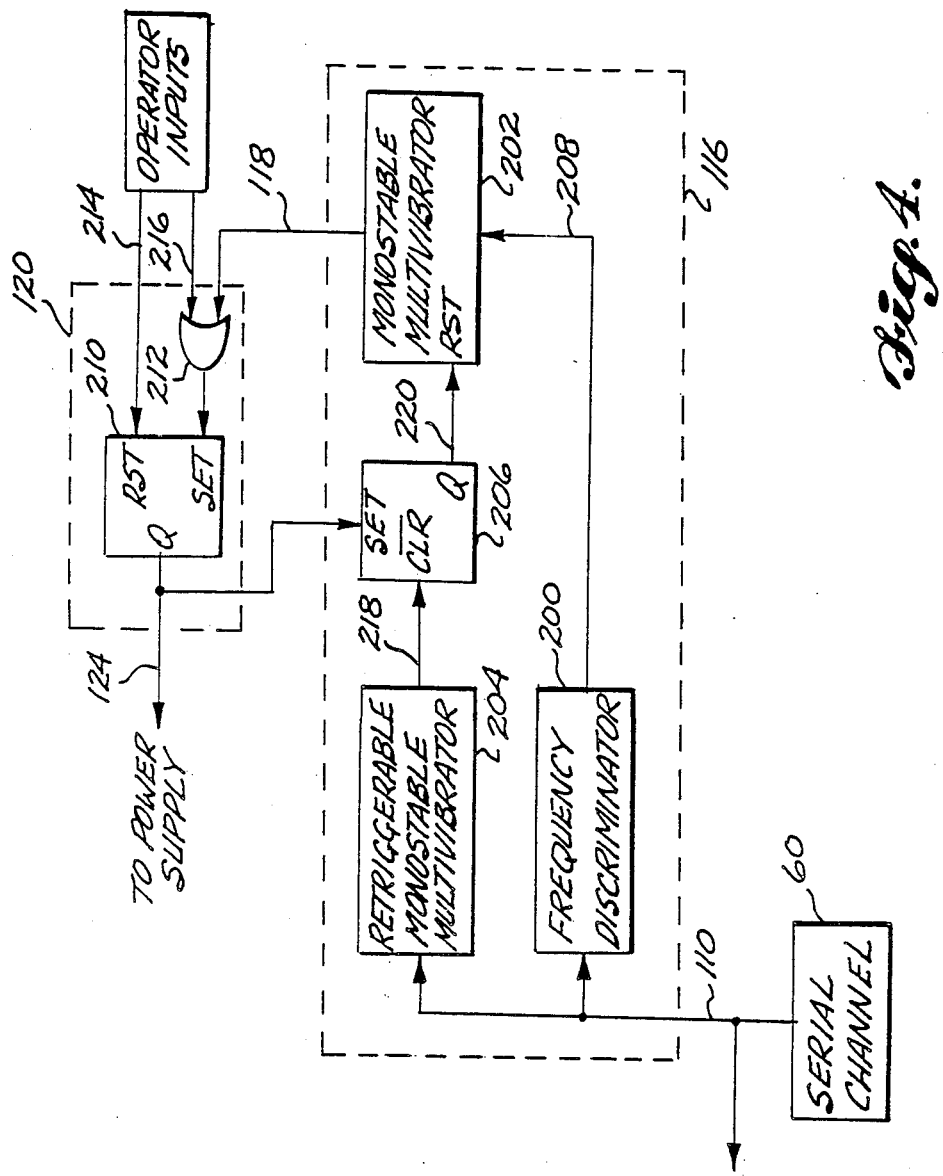
FIG. 4 is a block diagram of the 55 code detector and the ECG monitor on/off control.

FIG. 4 provides greater detail concerning 55 code detector 116 and on/off control 120. 55 code detector 116 comprises frequency discriminator 200, monostable multivibrator 202, retriggerable monostable multivibrator 204, and flip-flop 206. Serial data from serial channel 60 is input to frequency discriminator 200 via line 110. The frequency discriminator produces an output signal on line 208 whenever it detects four consecutive square wave pulses at a frequency corresponding to the serial transmission rate for serial channel 60. Thus where a serial transmission rate of 244 baud is used, frequency discriminator 200 would look for four consecutive cycles of a 122 Hz square wave, corresponding to one byte having a value of hex 55. When such a signal is detected on line 110, the resulting output signal on line 208 causes monostable multivibrator 202 to send a wake-up signal to on/off control 120 via line 118. On/off control 120 comprises flip-flop 210 and OR gate 212. When flip-flop 210 is set, the resulting high signal on line 124 causes the power supply to produce switched power on line 127 (FIG. 3), thereby turning the ECG monitor on. When flip-flop 210 is reset, the resulting low signal on line 124 causes the power supply to stop supplying switched power, turning the ECG monitor off. Flip-flop 210 can be reset, i.e., the ECG monitor can be turned off, by operator input via line 214 from switches 18 (FIG. 1). Flip-flop 210 can be set, i.e., the ECG monitor can be turned on, either by an operator input via line 216 or a wake-up signal via line 118. Therefore the appearance of a hex 55 byte on line 110 results in a wake-up signal on line 118 that sets flip-flop 210 and turns the ECG monitor on.

The 55 code detector shown in FIG. 4 includes a suppression circuit that enables an operator to turn the ECG monitor off while the defibrillator remains on. A suppression circuit is required because of the possibility that any byte of serial data could be equal to 55 hex. The wake-up circuit comprises retriggerable monostable multivibrator 204 and flip-flop 206. Retriggerable monostable multivibrator 204 continuously monitors the serial data on line 110 and produces an output signal on line 218 whenever such serial data is present or for a preestablished time (e.g., 100 milliseconds) after the disappearance of serial data. The signal on line 218 is input to the clear terminal of flip-flop 206, such terminal being active low. The output of flip-flop 210 on line 124 is input to the set terminal of flip-flop 206. Therefore whenever the ECG monitor is turned on, flip-flop 206 is set, resulting in a signal on line 220 that resets monostable multivibrator 202 and suppresses further wake-up signals. Additional wake-up signals can only be reenabled by turning off the defibrillator. A short time after the defibrillator is turned off, retriggerable monostable multivibrator 204 clears flip-flop 206, thereby removing the signal at the reset terminal of multivibrator 202.

Figure 5:
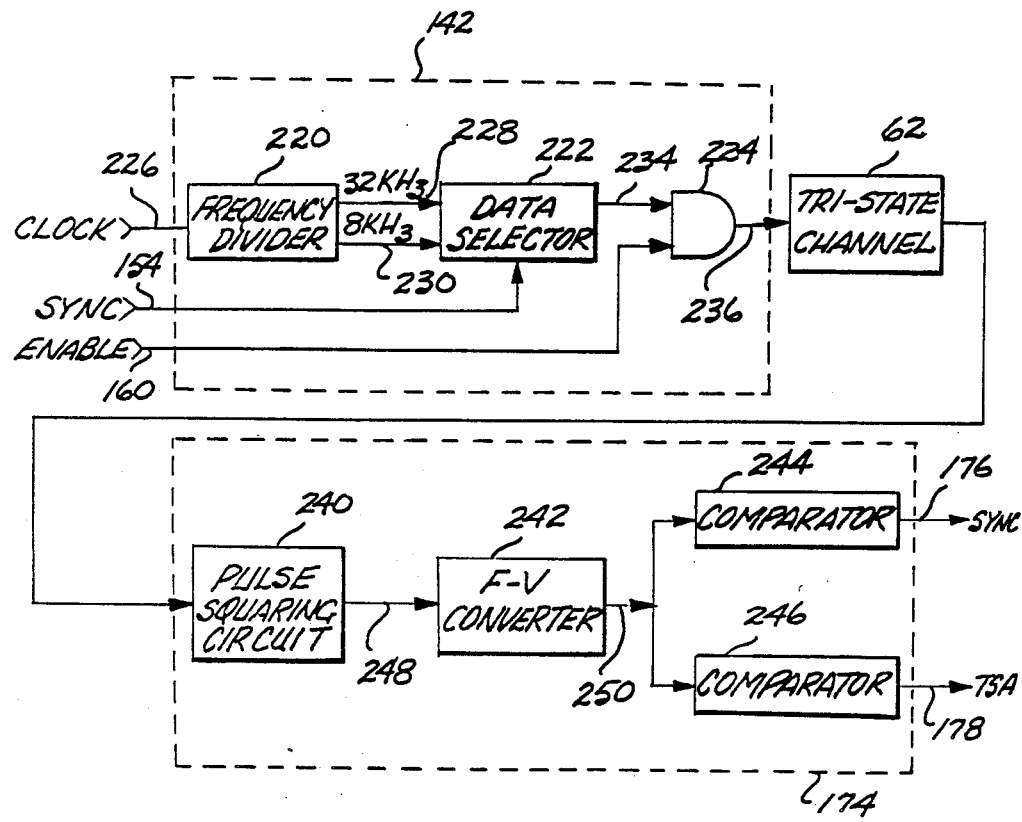
FIG. 5 is a block diagram of the tri-state modulator and demodulator.

The transfer of information via tri-state channel 62 is illustrated in greater detail in FIG. 5. As illustrated, tri-state modulator 142 comprises frequency divider 220, data selector 222 and gate 224. Frequency divider 220 is provided with a high frequency clock signal on line 226 that may, for example, be derived from executive microcomputer 112. The clock signal on line 226 is input to frequency divider 220, and the frequency divider divides the clock signal to produce a 32 kHz output signal on line 228 and an 8 kHz output signal on line 230. Data selector 222 selects either the 8 kHz or 32 kHz signal based on the sync signal on line 154, and outputs the selected signal on line 234. The selected signal on line 234 is one of the inputs to AND gate 224, the other input being the enable signal on line 160 from executive microcomputer 112. When the executive microcomputer determines that serial data is being received from the defibrillator, and that paddles have not been selected, the executive micro-computer holds line 160 high, such that the signal on line 234 is transferred through AND gate 224 and line 236 to tri-state channel 62. In this mode, the signal transmitted through the tri-state channel is either 8 or 32 kHz depending upon the sync signal on line 154. When serial data is being received and paddles have been selected, the executive microcomputer holds line 160 low, and a 0 kHz signal is transmitted through the tri-state channel. When serial data is not being received from the defibrillator, the executive microcomputer issues a command to the ECG microcomputer, via line 156 (FIG. 3), that prevents the ECG microcomputer from issuing sync pulses on line 154. As a result, data selector 222 always selects the 8 kHz signal for output on line 234. In this mode, the executive microcomputer selects a 0 or 8 kHz signal on line 236 by holding the enable signal on line 160 low or high respectively. The executive micro-computer holds 160 low when paddles have not been selected as the ECG signal source, thereby providing a 0 kHz signal to tri-state channel 62. However, when paddles have been selected, the executive microcomputer holds line 160 high, resulting in an 8 kHz signal being transmitted through the tri-state channel.

Demodulator 174 of defibrillator 12 comprises pulse squaring circuit 240, F-V (frequency to voltage) converter 242 and comparators 244 and 246. The signal received through tri-state channel 62 is input to pulse squaring circuit 240. The pulse squaring circuit compensates for any signal degradation present in the tri-state signal, and produces a corresponding signal on line 248 that is input to F-V converter 242. F-V converter 242 may comprise a phase lock loop or any equivalen device that produces an output signal on line 250 that has a magnitude corresponding to the frequency of the input signal on line 248. The signal on line 250 is input to comparators 244 and 246. Comparator 244 compares the signal on line 250 to a voltage that corresponds to a frequency intermediate between 8 and 32 kHz and outputs the resulting sync signal on line 176. Comparator 246 compares the signal on line 250 to a voltage that corresponds to a frequency between 0 and 8 kHz, to produce the tri-state active signal on line 178. Therefore when the defibrillator is on and a sync signal is being sent to the defibrillator via the tri-state channel, line 176 is either high or low depending upon whether the tri-state signal has a frequency of 32 or 8 kHz respectively. In this mode of operation, the tri-state active signal on line 178 is always high. However, when the defibrillator is off, the tri-state active signal on line 178 is either high (present) or low (not present) depending on whether an 8 or 0 kHz signal is being transmitted via the tri-state channel.

Figure 6:
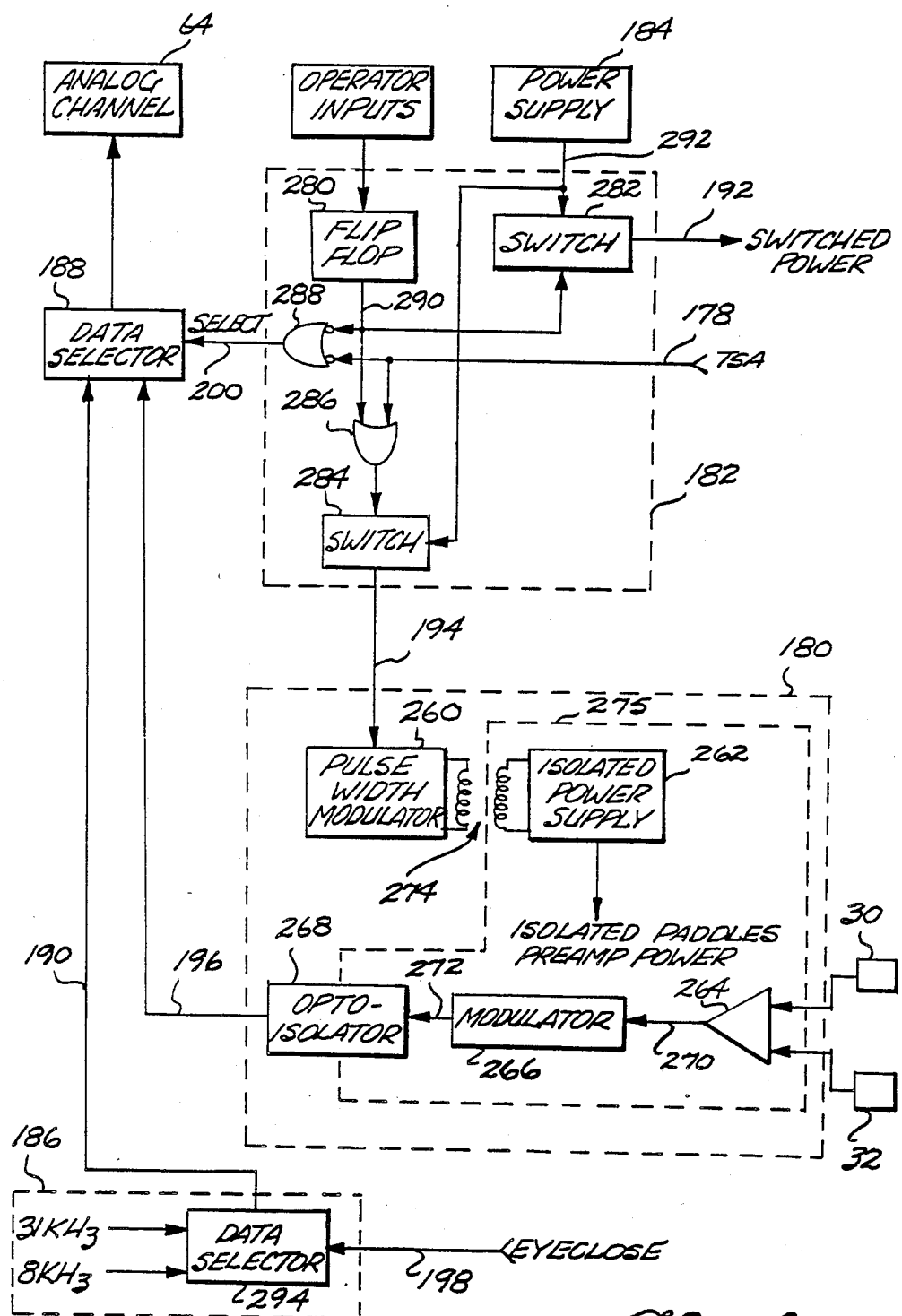
FIG. 6 is a block diagram of the paddles preamp, defibrillator on/off control, eyeclose modulator, and data selector.

Paddles preamp 180 and on/off control 182 are illustrated in greater detail in FIG. 6. Paddles preamp 180 comprises pulse width modulator 260, isolated power supply 262, differential amplifier 264, modulator 266, and opto isolator 268. The ECG signal from paddle electrodes 30 and 32 is input to differential amplifier 264 and the resulting amplified signal is input to modulator 266 via line 270. Modulator 266 may comprise a phase lock loop or similar circuit that produces an output signal on line 272 having a frequency corresponding to the magnitude of the voltage signal on line 270. Modulator 266 preferably produces a signal on line 272 that varies in frequency over the range 10–20 kHz in response to changes in the signal on line 270. The frequency modulated signal on line 272 is passed through opto isolator 268 and is output on line 196. Power is supplied to the paddles preamp from on/off control 182 via line 194. The power received on line 194 is isolated by means of a power converter that comprises pulse width modulator 260, isolated power supply 262 and transformer 274. Isolated power supply 262, modulator 266 and differential amplifier 264 therefore comprise a electrically isolated circuit 275 that provides DC isolation for paddle electrodes 30 and 32.

On/off control 182 comprises flip-flop 280, switches 282 and 284, and gates 286 and 288. Flip-flop 280 may be toggled between its two states by operator inputs from switches 34 (FIG. 1). The two flip-flop states correspond to the defibrillator being on and off. The output of flip-flop 280 on line 290 is connected to switch 282 and to gates 286 and 288. When the defibrillator is on, the signal on line 290 closes switch 282, such that unswitched power from power supply 184 via line 292 is connected to switched power line 192, thereby providing switched power to the various defibrillator components. Power to paddles preamp 180 is provided from power supply 184 via line 292, switch 284 and line 194. Switch 284 is closed, via OR gate 286, as a result of a "defibrillator on" signal from flip-flop 280 on line 290, or in response to the presence of the tri-state active signal on line 178. Therefore, the paddles preamp is powered when the defibrillator is on, or when the defibrillator is off and the tri-state active signal is present (i.e., paddles have been selected).

The output of flip-flop 280 on line 290 is also input to gate 288, the other input to gate 288 being the tri-state active signal on line 178. The output of gate 288 is the select signal on line 200 that controls data selector 188. The data selector receives as inputs the modulated eyeclose signal on line 190 or the modulated ECG signal on line 196. As indicated in the lower left-hand portion of FIG. 6, eyeclose modulator 186 comprises data selector 294 to which input signals of a 8 kHz and 31 kHz are provided from an appropriate clock and/or frequency divider circuit. Data selector 294 selects the 31 kHz signal for output onto line 190 when eyeclose pulse is received on line 198, and selects the 8 kHz signal at all other times. Data selector 188 selects either the ECG signal on line 196 or the modulated eyeclose signal on line 190 depending upon the select signal output by gate 288. The select signal will be high, and the ECG signal on line 196 will be selected, whenever the signal on either line 290 or 170 is low, i.e., whenever the defibrillator is off or whenever the tri-state action signal is not present. The eyeclose signal on line 190 will therefore be selected only when the defibrillator is on and the tri-state active signal is present. This latter state exists when and only when sync pulses are being transmitted through the tristate channel.

Figure 7:
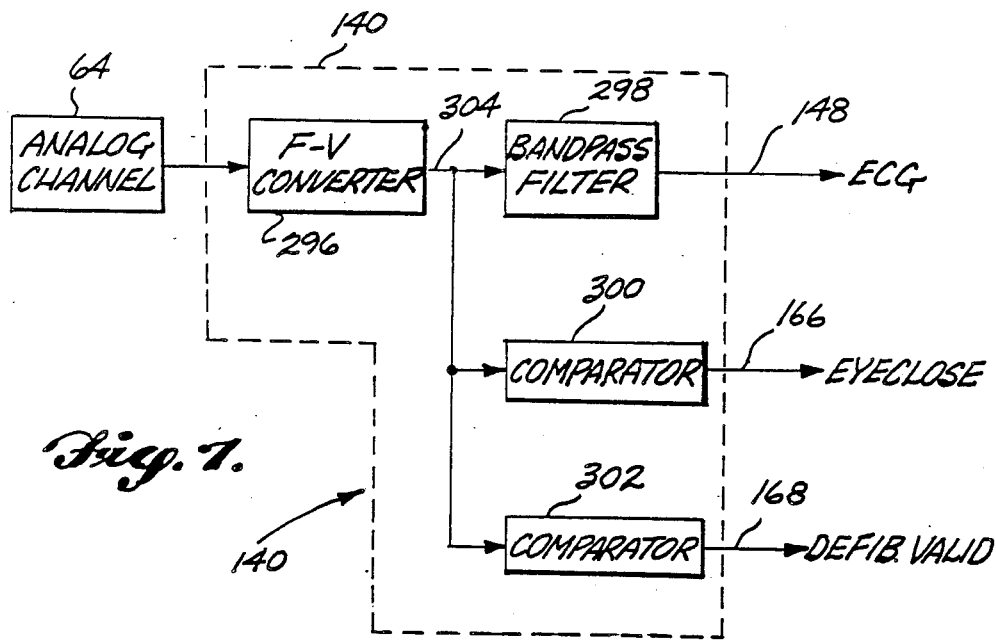
FIG. 7 is a block diagram of the analog channel demodulator.

FIG. 7 provides further details concerning demodulator 140. As illustrated, demodulator 140 comprises F-V (frequency to voltage) converter 296, bandpass filter 298 and comparators 300 and 302. The ECG or eyeclose signal received through analog channel 64 is input to F-V converter 296 that produces an output signal on line 304 that has a voltage corresponding to the frequency of the analog channel signal. The signal on line 304 is input to bandpass filter 298 and to comparators 300 and 302. Bandpass filter 298 filters the signal on line 304 in a conventional manner to produce the ECG signal on line 148. Comparator 300 compares the signal on line 304 to a voltage level that represents a frequency above the modulation range (e.g., 10–20 kHz) of the ECG signal but below the 31 kHz signal representing an eyeclose pulse. Comparator 30 thereby produces an eyeclose signal on line 166 that goes high during the interval in which an eyeclose pulse is received through the analog channel. Finally, comparator 302 compares the signal on line 304 to a voltage that represents a frequency between 0 kHz and the low eyeclose frequency of 8 kHz, to produce the defib valid signal on line 168 that is used by the executive microcomputer, as previously described, to determine whether any information is being received via the analog channel.

While the preferred embodiments of the invention have been illustrated and described, it should be understood that variations will be apparent to those skilled in the art. Accordingly, the invention is not to be limited to the specific embodiments illustrated and described, and the true scope and spirit of the invention are to be determined by reference to the following claims.

The embodiments of the invention in which an exclusion property or privilege is claimed are defined as follows:

1. A physiological instrument including a first component comprising an ECG monitor and a second component comprising a defibrillator, each component comprising means for permitting an operator to turn the component on and off, the components being adapted for integrated operation wherein information concerning defibrillator operation is transmitted from the defibrillator to the ECG monitor, the defibrillator comprising means for generating a power-on signal when the defibrillator is turned on and means for transmitting the power-on signal to the ECG monitor, and the ECG monitor comprising means for receiving the power-on signal and means responsive to receipt of the power-on signal for turning the ECG monitor on.

2. The physiological instrument of claim 1, wherein the defibrillator comprises means for generating a first electrical power-on signal, phototransmitter means for converting the first electrical power-on signal into a corresponding optical signal, and a window through which the optical signal may be transmitted out of the defibrillator, and wherein the ECG monitor comprises a window through which the optical signal may be transmitted into the ECG monitor, photoreceiver means for converting the optical signal into a second electrical power-on signal corresponding to the first electrical power-on signal, and means responsive to the second electrical power-on signal for turning on the ECG monitor.

3. The physiological instrument of claim 1, wherein the means for generating a power-on signal comprises means for generating a digital power-on signal, and wherein the means for transmitting the power-on signal to the ECG monitor comprises means for transmitting the ditigal power-on signal from the defibrillator to the ECG monitor in serial form.

4. The physiological instrument of claim 3, wherein the means for generating the digital power-on signal comprises means for generating at least one byte having a hexadecimal value of 55.

5. The physiological instrument of claim 4, wherein the ECG monitor comprises a frequency discriminator operative to produce an output signal upon receipt of a preestablished number of square waves at the serial transmission rate.

6. The physiological instrument of claim 5, further comprising pulse forming means for generating a wake up signal upon receipt of the output signal, and on/off control means responsive to the wake up signal to turn the ECG monitor on.

7. The physiological instrument of claim 6, wherein the ECG monitor comprises suppression means for inhibiting the wake up signal after the ECG monitor has been turned on until the defibrillator has been off for a preestablished period of time.

8. The physiological instrument of claim 7, wherein the suppression means comprises means for sensing the presence or absence of the digital data transmitted by the defibrillator.

9. A physiological instrument including a first component comprising an ECG monitor and a second component comprising a defibrillator, the defibrillator comprising a pair of defibrillator electrodes, a power supply, shock means for delivering a defibrillation shock to a patient through the defibrillator electrodes, preamplifier means couplable to the defibrillator electrodes for deriving a first ECG signal from the defibrillator electrodes, transmission means for transmitting the first ECG signal to the ECG monitor, and control means for selectively applying power from the power supply to the preamplifier means based on a status signal received from the ECG monitor, the ECG monitor comprising analysis means having an input terminal and means for analyzing an ECG signal provided at the input terminal, signal selection means for permitting operator selection of the defibrillator electrodes as the source of the ECG signal, coupling means responsive to selection of the defibrillator electrodes for coupling the first ECG signal to the input terminal of the analysis means, and status means operative when the defibrillator electrodes have been selected for transmitting the status signal to the defibrillator such that the control means applies power to the preamplifier means.

10. The physiological instrument of claim 9 wherein the control means includes means for permitting an operator to turn the defibrillator on, wherein the defibrillator further comprises second transmission means operative when the defibrillator has been turned on for transmitting a power-on signal to the ECG monitor, and wherein the status means is operative to transmit the status signal only when the power-on signal is not present and the defibrillator electrodes have been selected.

11. The physiological instrument of claim 10 wherein the analysis means includes means for generating a sync signal corresponding to an R wave in the ECG signal provides at the input terminal, wherein the status means includes means for transmitting the sync signal to the defibrillator, and wherein the means for delivering a defibrillation shock includes means for controlling the timing of the defibrillation shock based upon the sync signal.

12. The physiological instrument of claim 11 wherein the status means is operative to produce and transmit to the defibrillator an interface signal having three states, the interface signal being in the first state when the power-on signal is not present and the defibrillator electrodes have not been selected and when the power-on signal is present and the defibrillator electrodes have been selected, the interface signal being in the second state when the power-on signal is not present and the defibrillator electrodes have been selected, and wherein the interface signal alternates between the second and third states when the power-on signal is present and the defibrillator electrodes have not been selected, the alternation between the second and third states comprising the sync signal.

13. The physiological instrument of claim 9 wherein the second component further comprises a pacemaker operative to produce an eyeclose signal, and wherein the transmission means is operative to transmit either the first ECG signal or the eyeclose signal to the ECG monitor, the fir ECG signal being selected for transmission to the ECG monitor whenever the defibrillator electrodes have been selected.

14. The physiological instrument of claim 13 wherein the ECG monitor further comprises second preamplifier means for deriving a second ECG signal from an ECG cable, wherein the coupling means comprises means for selecting either the first or second ECG signal for connection to the input terminal of the analysis means, and wherein the second preamplifier means is inoperative to produce the second ECG signal when the eyeclose signal is received by the ECG monitor.

* * * * *